(12) United States Patent
Adams, Jr.

(10) Patent No.: US 9,581,534 B2
(45) Date of Patent: Feb. 28, 2017

(54) TRIBOMETER

(75) Inventor: Robert C. Adams, Jr., Armada, MI (US)

(73) Assignee: TRIBIS ENGINEERING, INC., Armada, MI (US)

( * ) Notice: Subject to any disclaimer, the term of this patent is extended or adjusted under 35 U.S.C. 154(b) by 881 days.

(21) Appl. No.: 13/808,652

(22) PCT Filed: Jul. 11, 2011

(86) PCT No.: PCT/US2011/043526
§ 371 (c)(1),
(2), (4) Date: Jan. 7, 2013

(87) PCT Pub. No.: WO2012/006613
PCT Pub. Date: Jan. 12, 2012

(65) Prior Publication Data
US 2013/0098139 A1    Apr. 25, 2013

Related U.S. Application Data

(60) Provisional application No. 61/362,830, filed on Jul. 9, 2010.

(51) Int. Cl.
*G01N 3/56* (2006.01)
*G01B 11/06* (2006.01)
*G01N 19/02* (2006.01)

(52) U.S. Cl.
CPC ............ *G01N 3/56* (2013.01); *G01B 11/0616* (2013.01); *G01N 19/02* (2013.01); *G01N 2203/0647* (2013.01)

(58) Field of Classification Search
CPC .. G01N 3/56; G01N 19/02; G01N 2203/0647; G01N 19/00; G01N 21/00; G01B 11/0616; G01B 11/00
USPC ....................................... 356/237.2
See application file for complete search history.

(56) References Cited

U.S. PATENT DOCUMENTS

| | | | | |
|---|---|---|---|---|
| 4,651,091 A | * | 3/1987 | Chambers | G01N 3/56 324/204 |
| 4,966,030 A | | 10/1990 | Kobayashi et al. | |
| 5,127,736 A | * | 7/1992 | Neiheisel | C21C 5/441 356/602 |
| 5,257,564 A | * | 11/1993 | Janowski | B24D 18/00 76/104.1 |
| 5,361,308 A | * | 11/1994 | Lee | G01B 11/2441 348/131 |

(Continued)

OTHER PUBLICATIONS

Keyence, CCD Laser Displacement Sensors, Super Precision/High Accuracy/Long Distance Innovative CCD Laser Displacement Sensors, Copyright 2006.

(Continued)

*Primary Examiner* — John Fitzgerald
*Assistant Examiner* — Truong Phan
(74) *Attorney, Agent, or Firm* — Brooks Kushman, P.C.

(57) ABSTRACT

A test apparatus and methods of measuring wear of a material with a laser displacement measurement apparatus based upon displacement of a test sample of the material or the wear of a testing surface and a specimen. A lubricant test method and apparatus measures the thickness of a lubricant film between two test surfaces by comparing the location of the test surfaces at rest and dynamically.

9 Claims, 6 Drawing Sheets

(56) References Cited

U.S. PATENT DOCUMENTS

| | | | |
|---|---|---|---|
| 5,422,703 A * | 6/1995 | Horie | G01B 11/02 356/445 |
| 5,777,745 A * | 7/1998 | Zeng | G01B 11/00 356/28 |
| 5,863,473 A * | 1/1999 | Ohsawa | G11B 5/8404 264/1.33 |
| 5,877,427 A * | 3/1999 | Trate | G01N 3/068 73/800 |
| 5,955,655 A | 9/1999 | Evans | |
| 5,965,896 A * | 10/1999 | Marton | G01N 3/46 250/559.22 |
| 6,145,370 A | 11/2000 | Evans | |
| 6,204,922 B1 * | 3/2001 | Chalmers | G01B 11/0616 356/630 |
| 6,251,983 B1 * | 6/2001 | Vogler | B60C 1/00 423/449.1 |
| 7,312,854 B2 | 12/2007 | Sugiyama et al. | |
| 7,489,410 B2 | 2/2009 | Nishio | |
| 7,639,373 B2 | 12/2009 | Torii et al. | |
| 7,639,374 B2 | 12/2009 | Torii et al. | |
| 7,667,857 B2 | 2/2010 | Nishio | |
| 2002/0041930 A1 * | 4/2002 | Erdemir | C23C 16/029 427/249.7 |
| 2002/0109111 A1 * | 8/2002 | Hall | G01B 11/0616 250/559.29 |
| 2007/0008841 A1 | 1/2007 | Seo et al. | |
| 2008/0094643 A1 | 4/2008 | Nishio et al. | |
| 2009/0158826 A1 * | 6/2009 | Leroux | G01N 3/42 73/81 |
| 2009/0244549 A1 | 10/2009 | Sakaguchi | |

OTHER PUBLICATIONS

Korean Intellectual Property Office, International Searching Authority, International Search Report and Written Opinion for corresponding PCT/US2011/043526 mailed Jan. 2, 2012.

* cited by examiner

TRIBOMETER

CROSS-REFERENCE TO RELATED APPLICATION

This application is the U.S. national phase of PCT Appln. No. PCT/US2011/043526 filed on Jul. 11, 2011, which claims the benefit of U.S. Provisional Application No. 61/362,830 filed on Jul. 9, 2010, the disclosures of which are incorporated in their entirety by reference herein.

TECHNICAL FIELD

This disclosure relates to test apparatus and methods of measuring wear of a material based upon displacement of a test sample of the material or the wear of a testing surface and a specimen. This disclosure also relates to a test apparatus and methods of testing the performance of a lubricant.

BACKGROUND

Tribology is the science of the interaction of surfaces in relative motion. It includes the study of friction, lubrication and wear. It is commonly applied to the design and development of bearings. A tribometer is used to measure the performance of materials relating to friction and wear when tested under different conditions, including pressure and velocity over time.

Several different types of tribometers have been developed including a pin on disk, oscillating, four ball, ball-on disk types. The duration of tribometer tests are frequently long and become a holding point in the development of new bearing material. ASTM standards emphasize the importance of test duration to obtain precise results. One example of an ASTM standard is provided below:

ASTM D3702-94 (2009) Standard Test Method for Wear Rate and Coefficient of Friction of Materials in Self-Lubricated Rubbing Contact Using a Thrust Washer Testing Machine:

The precision of wear measurement is relatively independent of test duration or amount of wear, but the precision of wear rate (calculation) improves with test duration and amount of wear. It is generally believed that useful wear rate precision requires the selection of test duration sufficient to produce 0.1 mm (0.004 in) of wear. Test durations will often be in the 50 to 4,000-h range.

One prior art technique involves a test apparatus in which a test surface moving at a selected velocity is contacted by a test sample while applying controlled pressure to the test sample. The test method requires a relatively long run-in period prior to beginning the data collection period. This run-in period is often a necessary step to ensure accurate results in tribology measurements. After a standardized time interval of many hours or days the test sample is removed from the apparatus and weighed to determine the rate of wear at the selected pressure and velocity. The test may include different intervals of constant velocity and pressure, and the difference in weight of the test sample from the beginning of the test interval to the end of the test interval indicates the amount of material lost during that test interval and thus gives the amount of wear achieved under the interval's velocity and pressure.

Similarly, another prior art technique involves a test apparatus in which a test sample contacts a rotating test surface. Again, a relatively long run-in period is required before beginning the test period. The test is conducted over a long period of time to permit the test sample to wear to an extent that is measurable reliably with a conventional measuring device. The test sample is again removed from the apparatus and the dimensions are taken to determine the rate of wear at the selected pressure and velocity. The difference in dimensions of the test sample from the beginning of the test to the end of the test indicates the amount of material lost during the test and gives the amount of wear achieved under the test parameters.

A dynamic measuring system is proposed in U.S. Pat. No. 4,966,030 in which a proximity sensor is attached to the supporting structure of the test sample to move with the test sample. The proximity sensor faces the wear surface disk and measures the change in distance between the supporting structure and the wear surface disk. A test is run in which pressure is applied to the test sample and the wear surface disk is rotated at a velocity to give the desired pressure and velocity over time. The difference in distance of the test sample from the beginning of the test to the end of the test indicates the amount of material lost during the test and gives the amount of wear achieved under the specific conditions. The system dynamically measures the change in the distance between the proximity sensor and the test surface. Measurements may be taken at various intervals while the test is conducted. The '030 patent also discloses a prior art pin-on-disk type wear testing device and method with reference to FIG. 3 of the patent.

Tribology testing in the field of lubricant testing presents different challenges than testing wear of a material. The thickness of the lubricant layer should be determined in lubricant testing. Optimal performance of a lubricant occurs when a system is operating at a hydrodynamic level in which a first test surface floats on a film of oil on a second test surface. A lubricant may also operate at a mixed level with surfaces partially touching through the film of oil and a minimum level of wear of the test surfaces. A third regime is boundary layer operation and the test surfaces are in contact that results in wear of the surfaces. There are longstanding problems with measuring the thickness of a lubricant layer dynamically and with sufficient accuracy to provide useful data relating to lubricant performance.

The apparatus and methods disclosed by applicant are intended to improve upon the prior art as described above. Applicant's reference to certain prior art techniques should not be construed as a representation that these are the only apparatus or methods or even that they are the most similar techniques.

SUMMARY

According to one aspect of the disclosure, an apparatus is provided for measuring wear of a test specimen that comprises a support structure that supports a test surface and a test specimen supported by a retainer on the support structure that engages the test surface. A drive operatively engages at least one of the test surface and the test specimen to move the test surface relative to the test specimen. A laser displacement measurement apparatus supported by the support structure reflects a laser off of a surface of the retainer, a surface of the test specimen, or a surface that moves with the test specimen to measure the displacement of the test specimen.

According to other aspects of the disclosed wear measurement apparatus, the laser displacement measurement apparatus may be a first laser displacement apparatus and a second laser displacement apparatus may be supported by the support structure that reflects a second laser off of the test surface, wherein the displacement measured by the first and second lasers are compared to correct for noise factors in displacement measurements. The second laser can also measure the transfer film thickness, as well as be the source for calculating lubricant film thickness versus the readings from the first laser. In other words, the transfer film thickness may be measured directly by the second laser, and lubricant film thickness calculated between the first and second laser. The third device may be a laser or other optical measuring device that can profile and measure a wear track. An optical profiling apparatus may be supported by the support structure that reflects an optical profiling system off of a wear track formed on the test surface by the test specimen, wherein the optical profiling apparatus measures the wear track on the test surface. The apparatus may be an optical profiling system selected from the group comprising a projection grid pattern system or a multiple beam laser displacement system.

According other aspects of the disclosure, the test surface may be a flat disk that is rotated in a first plane and the test specimen is moved by the retainer relative to the disk in a second plane that is parallel to the first plane. Alternatively, the test specimen may be a cylindrical sleeve and the test surface may be a cylindrical shaft that rotates within the cylindrical sleeve in an oscillating motion about an axis and the displacement of the sleeve and shaft may be measured by the laser displacement measurement apparatus.

The support structure may further include a load application system that applies a calibrated load P to the test specimen and the drive may include a variable speed control that moves the test surface at a calibrated speed V with the displacement of the test specimen being recorded as a wear rate W. The test specimen is sequentially subjected to a plurality of loads P at a plurality of speeds V to develop a plurality of wear rates W that may be mapped to develop a three dimensional wear rate map for a specimen. The energy E expended by the apparatus may be calculated as a product of P and V and the coefficient of friction F. The calibrated load P is applied and the drive is operated at the calibrated speed V until the wear rate is determined to be at a steady state within a predetermined regression coefficient value or other dynamic mathematical analysis. The wear rate value W is recorded for the values P and V and the test for that set of values P and V is completed, and the test specimen is subjected to a different combination of values P and V, repeatedly.

According to another aspect of the disclosure, a method of testing for wear is disclosed that comprises selecting a test specimen and selecting a test surface that is engaged by the test specimen at a load P. The test surface is moved relative to the test specimen at a speed V. A physical characteristic of the test specimen or test surface, such as the temperature, is monitored to determine whether the physical characteristic is at steady state to a predetermined extent. The displacement of the test specimen relative to a reference point is measured with a laser displacement measurement apparatus to dynamically calculate a plurality of wear rate values W at the values P and V. The wear rate values W are calculated in a dynamic mathematical analysis, for example in a regression analysis, to determine a value L. The value L is compared to a predetermined standard S and each test cycle is concluded for a selected load P and a selected speed V when L is acceptable relative to the standard S.

According to additional aspects of the disclosure as they relate to the method of wear testing, the laser displacement measurement apparatus is a first laser displacement measurement apparatus and a second laser displacement apparatus measures the displacement of the test surface relative to the reference point to calculate a base line value B and comparing the wear rate value W to the base line value B to correct for noise factors in the wear rate values W. A third laser displacement measurement apparatus, or optical profiling system, may reflect a third laser off of a wear track formed on the test surface of the disk by the test specimen. The third laser displacement measurement apparatus may be utilized to detect the profile of the wear track.

According to another aspect of the disclosure, an apparatus for testing a lubricant is provided that comprises a first test surface that is provided with a lubricant and a second test surface that is supported adjacent the first test surface with the lubricant being provided between the first and second test surfaces. A drive moves at least one of the first and second test surfaces relative to the other of the test surfaces. A laser displacement measurement apparatus is used to determine a film thickness value corresponding to the spacing between the first and second test surfaces dynamically while the drive moves the first and second test surfaces relative to each other.

The laser displacement apparatus may include a first laser that determines the location of a test sample that is pressed onto a stationary disk with no oil between the test sample and the disk. A second laser determines the location of the stationary disk. The disk is then rotated at a selected velocity with the selected load applied with oil supplied between the test sample and the disk with the oil being carried under the sample that raises the sample. The displacement of the sample relative to the disk is measured to provide an accurate representation of film thickness. The film thickness can be dynamically monitored and at the conclusion of a test cycle the pressure extrudes the oil from between the sample and the disk and the differential change indicates the loss of film thickness.

The apparatus for testing a lubricant may further comprise a controller that receives the film thickness value over time and compares the film thickness values received over time to determine whether the film thickness is remaining constant relative to a predetermined standard for a given load P and speed V that may be interpreted to indicate hydrodynamic operation of the lubricant. The controller may also correlate a change in the spacing between the first and second test surfaces dynamically while the drive moves the first and second test surfaces relative to each other over time to determine a wear rate of at least one of the surfaces.

The disclosure also comprehends a method of testing a lubricant that comprises selecting a first test surface and a second test surface and providing a lubricant between the first and second test surfaces. A load P is applied to the lubricant between the first and second test surfaces and moving the first and second test surfaces at a speed V. A physical characteristic of the lubricant, such as the temperature of the lubricant, is monitored to determine whether the physical characteristic is at steady state within a predetermined range. A plurality of film thickness values are measured with a laser displacement measurement apparatus dynamically over time that corresponds to the spacing between the first and second test surfaces while the drive moves the first and second test surfaces relative to each other.

The method of testing a lubricant may further comprise correlating the plurality of film thickness values to determine whether the film thickness in remaining constant and for a given load P and speed V. Alternatively, the of testing a lubricant may also be adapted to dynamically calculate a plurality of wear rate values W for a given set of load values P and speed values V. The wear rate values may be compared to a predetermined standard S to determine whether the wear rate W is linear. The test for a given load P and speed V may be terminated when the wear rate is linear.

The above aspects of the disclosure and other aspects will be apparent to one of ordinary skill in the art in view of the attached drawings and the following detailed description of the illustrated embodiments.

DETAILED DESCRIPTION

Figure 1:
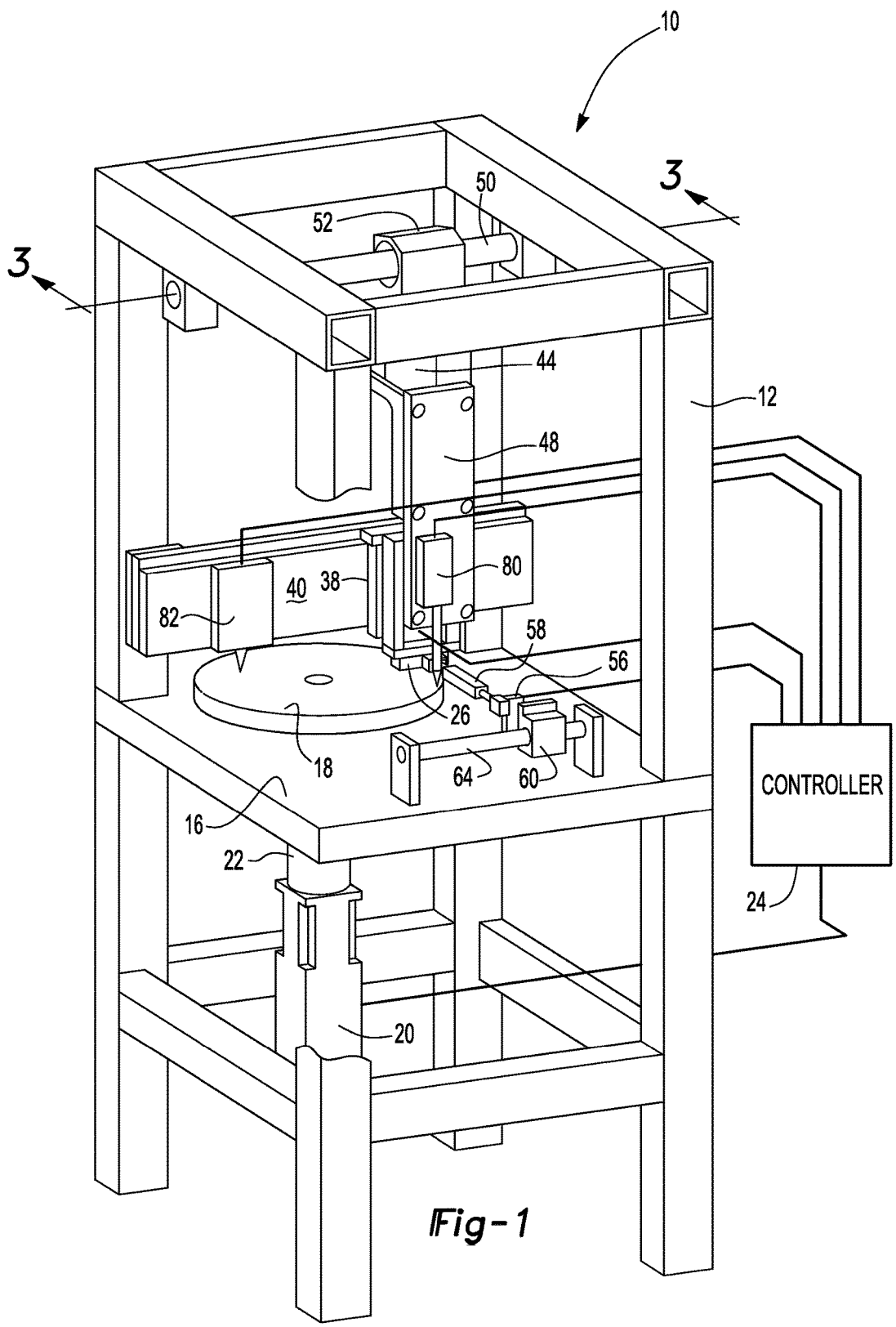
FIG. 1 is a perspective view of a tribometer made according to one embodiment of the present invention.

Referring to FIG. 1, a disk tribometer 10 is illustrated as one example of a tribometer that may be used to practice Applicant's invention. While a disk tribometer 10 is illustrated, the present invention may also be practiced with other types of tribometers such as a pin on disk tribometer, an oscillating tribometer, a four ball tribometer, a ball-on disk type tribometer, and others. Applicant's invention is generally applicable to tribometers in which wear is measured by determining the material removed as a function of displacement due to the dimensional change of the material experienced by loss of material during wear, and not specifically as a function of the reduction and mass of a sample. However, it should be understood that materials with a homogeneous density would have a relatively direct correlation to dimensional changes of material loss caused by wear and weight loss caused by wear.

The tribometer 10 includes a rigid frame 12 that supports a platform 16. Frame 12, as well as other components discussed below, makes up the support structure of the tribometer 10. A wear surface 18, or disk, is rotatable on the platform 16. A motor 20 is operative to rotate the wear surface 18 and is connected to the wear surface 18 by means of a bearing assembly 22. A controller 24 is electrically connected to the motor 20 to control the velocity, direction, and any frequency pulsations. The controller 24 may also control and record data relating to the load selected for a given test cycle. In another embodiment, the controller 24 may have data storage capability and may store data relating to operation of the motor over time. In one embodiment, the motor 20 is a servo motor that can be used to rotate the wear surface 18 at a controlled rate of speed so that an accurate sliding surface speed can be provided for wear testing.

The wear surface 18 may be formed of a material that has a coefficient of friction that is determined by testing, such as stainless steel. The wear surface 18 may also be formed of a material chosen to represent a real world application of what the sample material will be in sliding contact with in actual use, such as grey cast iron. The surface of the wear surface 18 may also have a specific finish or flatness. Depending upon the material or test to be conducted with the tribometer, the wear surface 18 may be selected from a wide range of materials having a known coefficient of friction, known surface profile, or known application. It should also be understood that the wear surface 18 need not be a metal.

Figure 2:
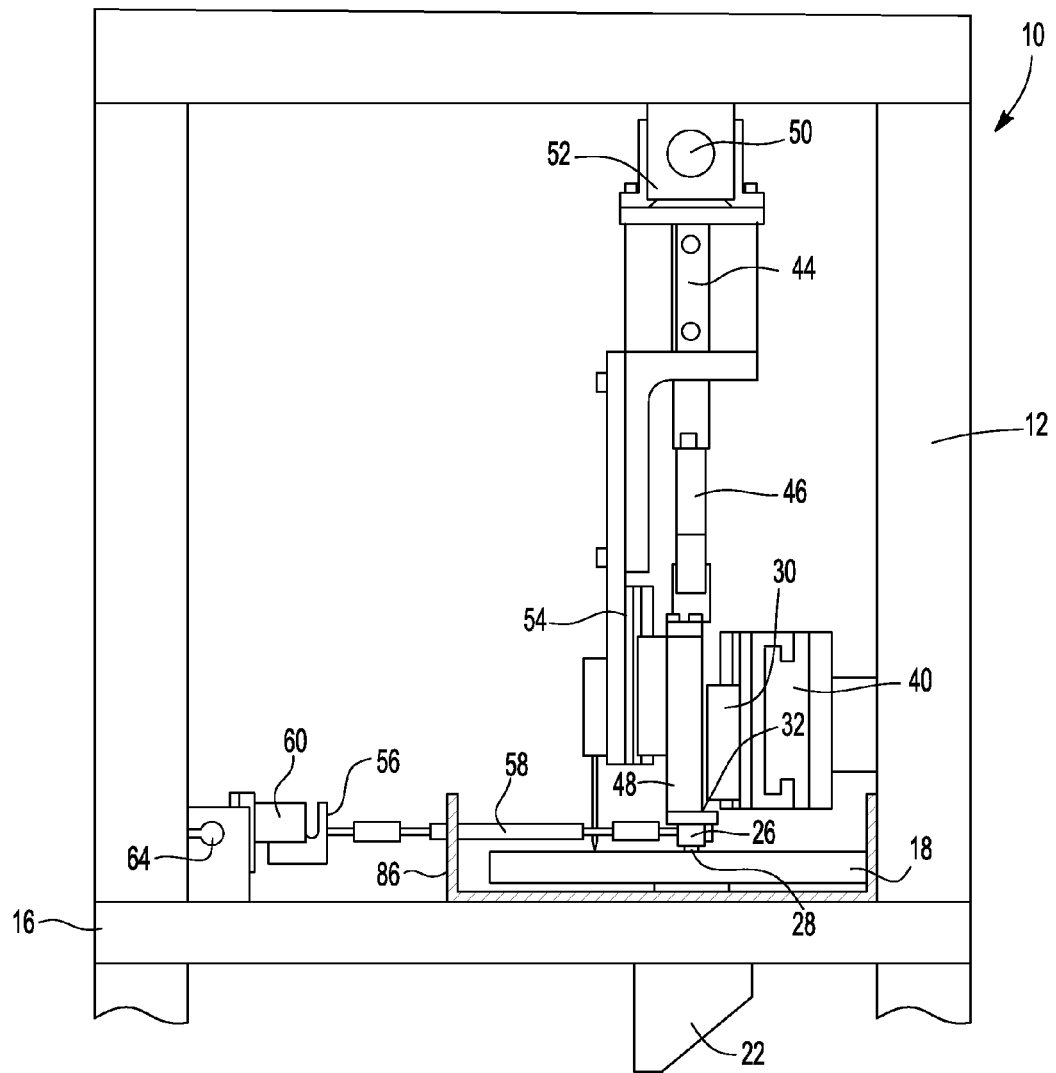
FIG. 2 is a fragmentary side elevation view of the embodiment of the tribometer shown in FIG. 1.
Figure 3:
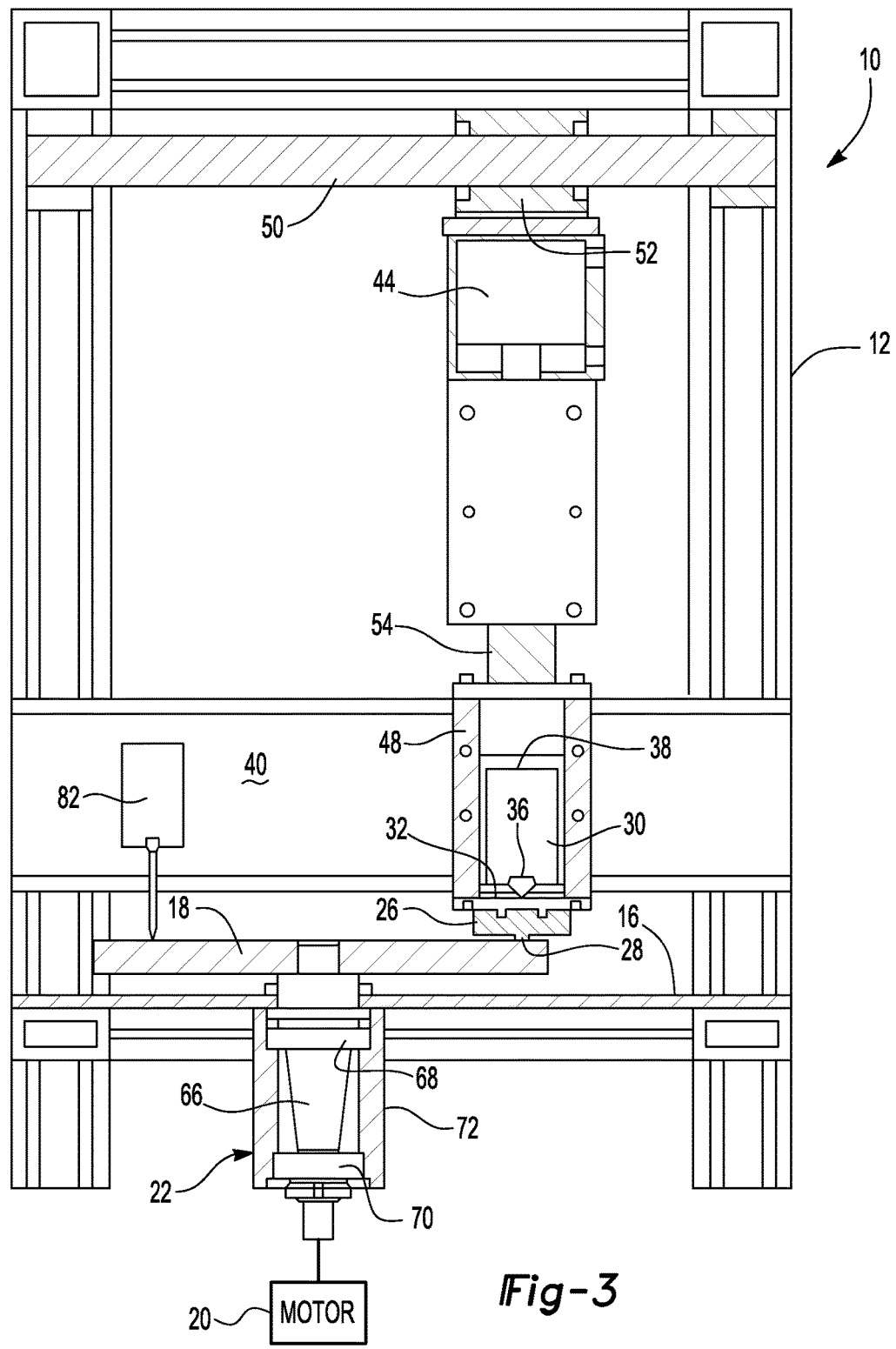
FIG. 3 is a cross-sectional view taken along the line 3-3 in FIG. 1.

A sample holding fixture 26 is provided to hold a test sample 28 (as shown in FIGS. 2 and 3) in engagement with the wear surface 18. The test sample 28 may be a plastic material, an elastomeric material, a metal, a composite, or any material that is intended to be tested for its performance of wear characteristics when in sliding contact with the chosen wear surface 18.

A precision laser measurement device, or laser measurement system 30, (as shown in FIGS. 2 and 3) is assembled to the frame 12 to be oriented relative to a reflection surface 32 (as shown in FIGS. 2 and 3) on the sample holding fixture 26. The precision laser measurement device 30 uses laser triangulation to measure distance. The laser beam 36 emitted by the laser measurement system 30 is used to measure the distance to the reflection surface 32 and the reflected light is detected, in this example by a charge coupled device (CCD) as the test sample 28 wears. While a CCD is the most common approach and is well-suited to this application, other laser based measurement methods may be used provided that they can offer similar accuracy. The laser measurement system 30 is contained within a laser housing 38. The laser measurement system 30 and laser housing 38 are secured to a cross slide 40 that extends horizontally across the frame 12 in the illustrated embodiment. The position of the laser housing 38 on cross slide 40 may be set using sensors (not shown) and motor drives (not shown) in a fully automatic embodiment of the tribometer. Cross slide 40 may be vertically oriented if the wear surface 18 were to be horizontally oriented in alternative embodiments of the invention. The laser measurement system 30 is connected to controller 24 which in yet another embodiment of the invention has data storage capability and stores the data received from the CCD laser over time. It should also be understood that other forms of lasers or light emitting devices with similar precision within the appropriate measurement ranges, similar accuracy, and similar sampling rates to that of the CCD laser could also be used.

The laser measurement system 30 reflects one or more laser beams 36 (as shown in FIG. 3) off of the sample holding fixture 26. Wear of the test sample 28 is measured by measuring the movement of the sample holding fixture 26 relative to the laser measurement system 30 that is assembled to the frame 12. Wear in the test sample 28 may be measured by the laser measurement system 30 even if the wear is on the order of 10 nanometers.

Referring to FIGS. 1-3, a load cylinder 44 is coupled with an applied load cell 46 and assembled to a load frame 48 to apply a load to the sample holding fixture 26. The load cylinder 44 applies a load or force through the load cell 46 and load frame 48 to the test sample 28. The test sample 28 is retained in a sample holding fixture 26. The applied load cell 46 measures the load applied and provides data regarding the load over time to the controller 24.

In one embodiment the load cylinder 44 is also electrically connected to controller 24 and controller 24 may be used to actuate load cylinder 44 to a predetermined load, change the loading at set intervals, or oscillate the load during the test. In another embodiment, the applied load cylinder 44 is controlled by a proportional regulator system provided by the controller 24 in which proportional pressure is determined through feedback from the applied load cell 46. Proportional-integral-differential (PID) control loop software may be used to accomplish a proportional pressure. Continuous PID control of pressure allows the system to control the pressure applied by the load cylinder 44 and thereby maintain the load applied to the test sample 28 at the desired level.

A cross load bearing shaft 50 supports a load bearing 52 that is also attached to the load cylinder 44. The load cylinder 44 and applied load cell 46 are movable along the load bearing 52. Load may be maintained on the test sample 28 while test sample 28 is moved across the wear surface 18. The position of the load bearing 52 on the load bearing shaft 50 may be set using sensors (not shown) and motor drives (not shown) in a fully automatic embodiment of the tribometer.

A vertical slide 54 is provided on the load frame 48 to allow load frame 48 to move as the test sample 28 wears. The load frame 48 supports the sample holding fixture 26 and is operatively connected between the load cylinder 44, applied load cell 46 and sample holding fixture 26. The position of the load frame 26 may also be adjusted in a vertical direction as shown in the drawings to accommodate variations in sample size and the position of the load cylinder 44.

A friction load cell 56 is linked between a turnbuckle linkage 58 and a cross friction bearing assembly 60. Friction load cell 56 measures the frictional force applied to the test sample 28 and can provide data relating to the friction applied to the test sample 28. Friction load cell 56 is electrically connected to controller 24. In one embodiment of the invention, controller 24 has data storage capability and frictional force data over time may be stored. A bearing (not shown) is received on a cross friction bearing shaft 64. The bearing (not shown) moves horizontally with the test specimen 28 as it is moved laterally or horizontally across the wear surface 18. The turnbuckle linkage 58 adjusts the distance between the cross friction bearing shaft 64 and sample holding fixture 26. The turnbuckle linkage 58 is adjusted to maintain the load cylinder 44, applied load cell 46 and load frame 48 in alignment perpendicular to the wear surface 18.

The cross friction bearing assembly 60 includes the cross load bearing (not shown) and the cross friction bearing shaft 64 to allow the load and measurement components to move to different radial distances over the shape rotating wear surface 18. The position of the bearing (not shown), cross friction bearing shaft 64 and laser cross slide 40 may be set using sensors (not shown) and motor drives (not shown) in a fully automatic embodiment of the tribometer. As well, sensors (not shown) and motor drives (not shown) may be coordinated so as to move load bearing 52 on cross load bearing shaft 50, laser housing 38 on cross slide 40, and cross friction bearing assembly 60 on cross friction bearing shaft 64 at the same time to allow for coordinated radial movement of test sample 28 on wear surface 18 during testing.

The load cylinder 44 is assembled to the cross load bearing shaft 50 by the load bearing 52. The cross load bearing shaft and load bearing 52 hold the load cylinder 44 in vertical alignment so that all the frictional force applied to the test sample 28 may be measured by the friction load cell 56.

Referring to FIG. 3, the motor 20 and bearing assembly 22 are shown in greater detail. The motor provides torque through the bearing assembly 22 to the wear surface 18. A spindle 66 is journaled between an upper bearing 68 and a lower bearing 70. The spindle 66, upper bearing 68 and lower bearing 70 are all contained within a bearing housing 72. The bearing housing 72 is secured to the platform 16 in a fixed location. The upper bearing 68 and lower bearing 70 allow the wear disk 18 to rotate freely even as a load is applied to the test sample 28.

The planar motion between the test sample and the wear surface may be a constant velocity, a changing velocity, a constant acceleration, a changing acceleration, a series of stops and starts, or an oscillating motion. Either the wear surface 18, through rotation, or the test sample 28, through horizontal cross movement of the sample holding fixture 26, may be moved to change the relative velocity, acceleration or oscillation.

Figure 4:
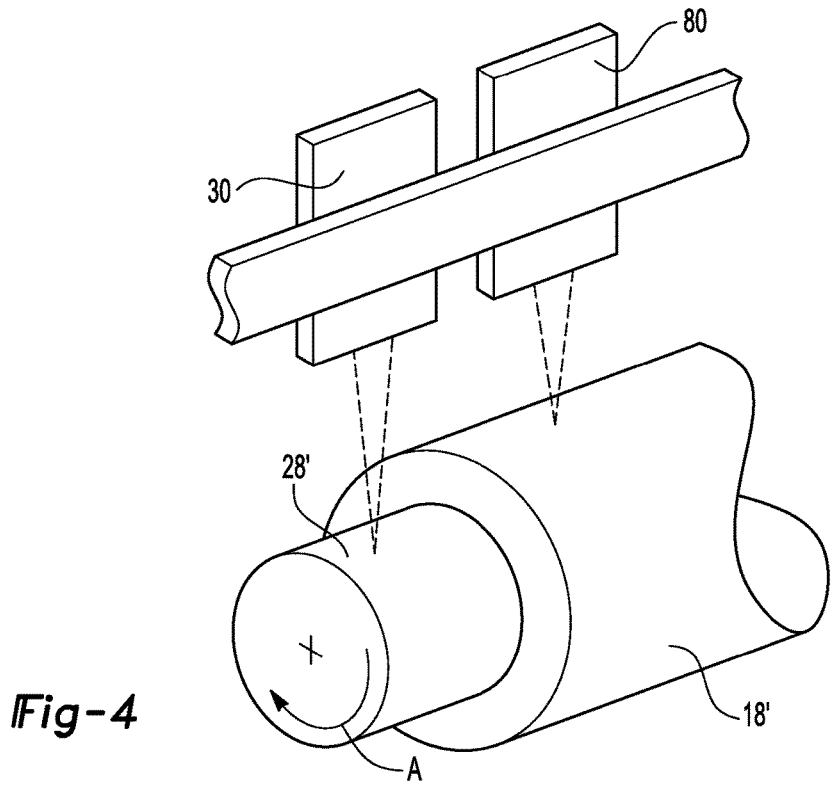
FIG. 4 is a diagrammatic view of a shaft rotating within a sleeve to be measured with a rotating tribometer set-up.

Wear of rolling element contacts may also be measured with this invention, as illustrated diagrammatically in FIG. 4. A cylindrical sleeve wear surface 18' and a cylindrical shaft test sample 28' are shown with the shaft test sample 28' rotating within the cylindrical sleeve wear surface 18'. A load may be applied to the shaft test sample 28' and the shaft test sample 28' may be rotated as indicated by the arcuate arrow "A". A first laser 30 and a second laser 80 may be directed to the outer surface of the sleeve wear surface 18' and the shaft test sample 28'. Alternatively, rotational motion may be applied to a series of ball bearings in a cup or other retainer with displacement being measured in a similar manner. The laser measurement system may be used to measure ball wear and friction as described above with the laser measurement system 30 being oriented to reflect the laser beam off of a portion of the cup or retainer that retains the ball bearing during the wear testing operation.

Figure 5:
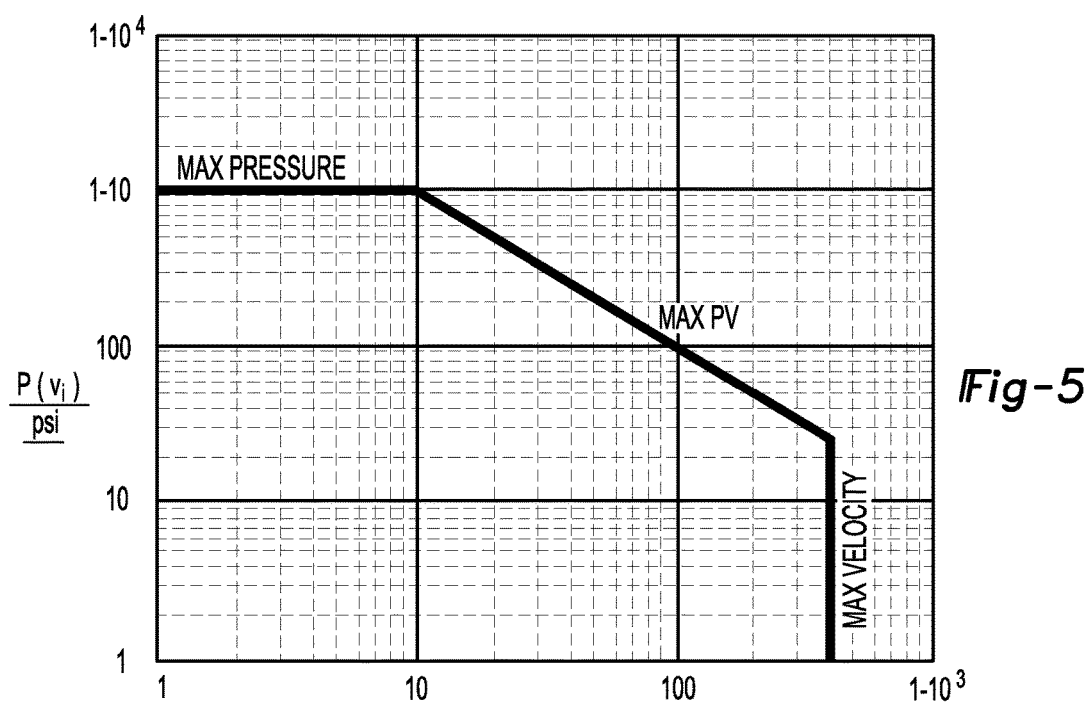
FIG. 5 is a graph of a two-dimensional pressure-velocity model.

Wear of bearing materials or plain bearings has long been approximated by a pressure as a function of velocity model (PV). The PV model is used to determine the wear rates and acceptable energy limits for plain bearing materials. An example of a two-dimensional PV model can be seen in FIG. 5. The PV limit is assumed to be the acceptable value of power per unit area that can be dissipated by plain bearing material. Operation above the PV limit is predicted to cause bearing failure. Operating below the PV limit is normally assumed to be proportional to the wear rate at the limit. Based upon the above assumptions, it is estimated that if a bearing is operated at half the PV limit of a bearing then wear is estimated to be half of what it would be at the PV limit. This indicator of bearing performance is used to determine the acceptability of a bearing application. As a common practice, bearing manufacturers supply graphical representations of maximum PV that specify the maximum pressure and the maximum velocity as a maximum level of each and a linear function that is specified as max PV, and wear is estimated from such a chart based on the anticipated application. However, two-dimensional PV models are a poor indicator of actual bearing performance.

Figure 6:
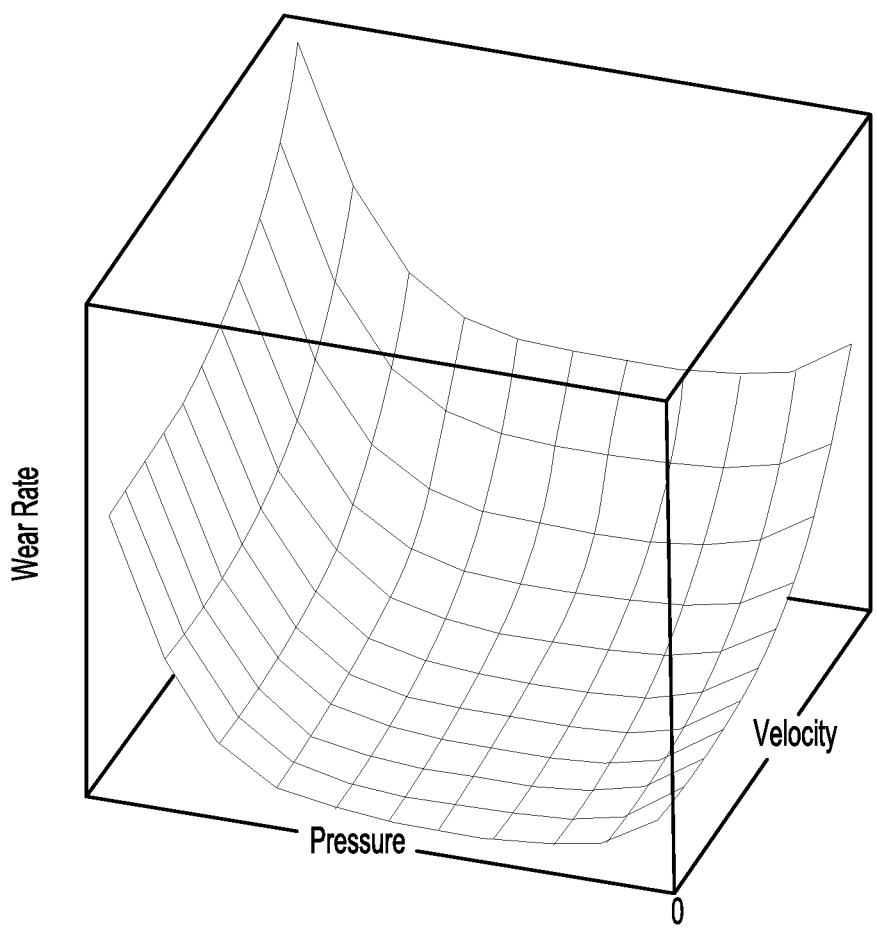
FIG. 6 is a graph of a three-dimensional pressure-velocity wear map.

It has been found that the pressure/velocity function for plain bearings is better represented as a three-dimensional model. An example of a three-dimensional PV wear map may be seen in FIG. 6. The coefficient of friction is generally much higher at light loads than at heavy loads. Further, higher friction for light loads results in wear that is higher than would normally be predicted by a two-dimensional PV model. For long life applications, higher friction at light loads may lead to premature bearing failure. At low sliding velocities, wear tends to be purely adhesive in nature and is not predicted by wear energy absorption as represented by the PV model.

In practice, the PV curve for a given material is often defined by three or four points. In most cases, PV is held constant and the few collected data points are presented as a function of the remaining variable. Since current testing techniques may require, for example, 150 to 200 hours to achieve a measurable amount of wear, few data points are collected and the two-dimensional PV model is still relied upon even though it is known to be inaccurate. Applicant's test method provides rapid test results that facilitate material and surface tribology coefficients to be characterized much quicker. The test method dynamically measures wear and friction and delivers both raw and analyzed data from the test. According to Applicant's method, the laser measurement device, such as laser measurement system 30 shown in the embodiment above, is used to dynamically measure displacement in the range of nanometers. The test begins by providing a brief run-in period in which the test system measures steady-state wear. The system monitors displacement, friction and temperature rise. When the coefficient of friction, the temperature rise and the rate of change of displacement become constant, then the test determines that the system is in steady-state. At this point, the values of coefficient friction, wear rate and energy absorption may be recorded. The tribometer system then may increment the velocity and applied pressure to develop a characteristic three-dimensional map that covers the entire useful range of operation for the material. The system is intended to detect operational and catastrophic failure of the bearing material. If any of the monitored characteristics begin to cascade or increase unacceptably, then the extreme operational limit of the bearing material is determined to have been reached. The CCD laser tribometer system is used to collect data. A mathematical model of the relationship between the pressure and velocity input variable is developed that relates the input variables to the output characteristics of wear as measured by the system. The system then records the data and calculates coefficient that describe the wear characteristics.

Current test systems, such as the pin-on-disk test utilize a rotating disk against which a pin or material is pressed while a disk is rotated. Wear of both the pin and the disk are generally observed and recorded. Due to the length of time required to conduct the test, wear of the disk must be accounted for. However, with a short duration test as disclosed in this application, in a pin-on-disk test, wear of the pin may be measured while wear of the disk may be negligible and assumed to be zero. To illustrate, consider a relatively soft test sample 28 used in conjunction with a hard, solid wear surface 18. In a case such as this, only a small nanometer range level of wear in the test sample would cause even a less negligible or near-zero amount of wear on the wear surface 18.

The servo motor 20 drives the wear surface disk 18 to ensure precise velocity control. The test sample 28 is held in a frame that presses it against the wear surface 18. The pneumatic cylinder applies a specified level of force to the test sample. The load cylinder 44 and applied load cell 46 are part of a force control loop that measures the force applied to the test sample 28. A predetermined and accurately controlled force is applied to the test sample 28.

The system may include two thermal sensors (not shown) that are mounted in the system. One thermal sensor is mounted within the sample frame immediately adjacent to the test sample 28. The other thermal sensor is mounted on the machine in a location that is not substantially affected by operation of the system and provides an ambient temperature. The temperature rise of the thermal sensor adjacent to the test sample 28 is compared to the ambient temperature and is monitored during the course of the test. A friction load cell 56 is mounted through a turnbuckle linkage 58. The linkage is mounted tangentially to the disk motion at the point of contact. The frame does not resist motion in the tangential direction by anything except the load cell linkage. The load cell linkage directly measures the frictional force. The ratio of the frictional force to the applied force is determined to be the coefficient of friction.

$$\mu = \text{Force}_{Friction}/\text{Force}_{Applied}$$

The laser measurement system 30 is secured to the cross slide 40. The CCD laser reflects the laser beam 36 off of the sample holding fixture 26. The laser beam is then received in the laser measurement system 30 that calculates the displacement of the sample frame. The CCD laser is able to measure the actual wear of the test sample 28 to a resolution of about 10 nm. The laser measurement system 30 is mounted to a micrometer adjustable vertical slide on the cross slide 40.

Figure 7:
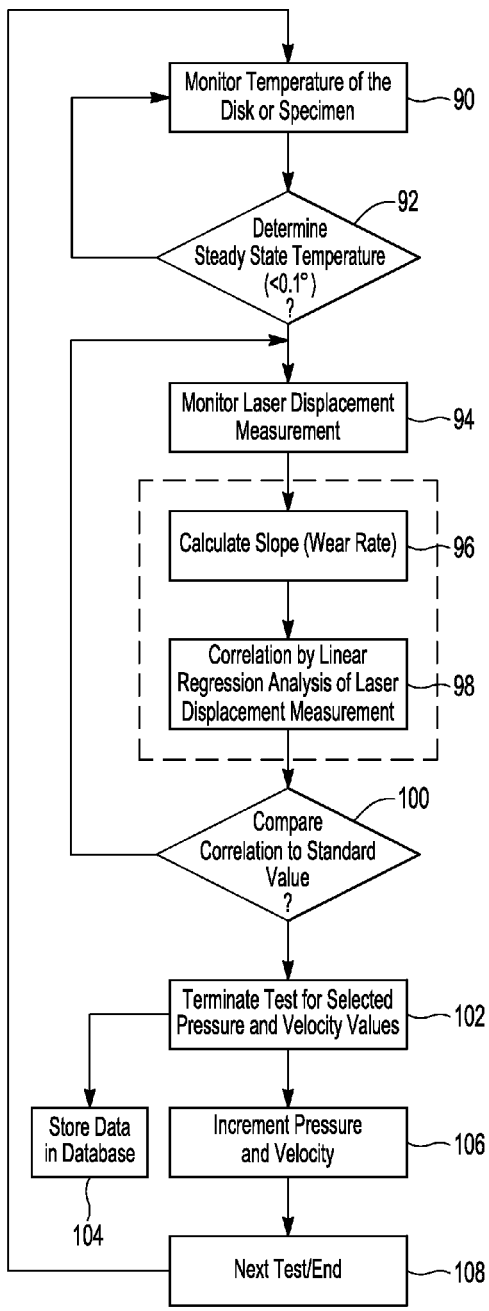
FIG. 7 is a flow chart illustrating one embodiment of a method of wear testing.

Referring to FIG. 7, a test procedure for testing the wear rate of a material is illustrated with a flow chart. It should be understood that many other different test procedures may be developed within the spirit and scope of Applicant's invention. The method begins by monitoring the temperature of the disk or specimen at 90. The system determines whether a steady state temperature has been reached, for example, less than 0.1° C. variation in temperature, is processed at 92. If steady state has not been reached, the system continues to monitor the temperature of the disk or specimen, at 90. Once steady state is reached, the system monitors laser displacement measurements, at 94, on a continuous or dynamic basis. The system calculates the slope or wear rate at 96 and may simultaneously correlate, at 98, by linear regression analysis or other mathematical analysis to determine the laser displacement measurement. The correlation, or other mathematical analysis, is compared to a standard value to determine whether a constant slope or wear rate standard has been met, at 100. If the slope or wear rate is not a linear function, the system continues to monitor the laser displacement measurement at 94. Once the correlation compares favorably to a standard value (or function), at 100, the system may terminate the test for a selected pressure and velocity values, at 102, and store the wear rate, pressure and velocity values in a database, at 104. The system may then increment the pressure and velocity values, at 106, to select a different pressure and/or velocity for the next dynamic testing cycle. If a next test is requested, at 108, the system returns to monitoring the temperature of the disk or specimen, at 90, and continues until all desired pressures and velocities have been tested. Once the specimen is tested for each of the selected series of pressure and velocity values, the test may be concluded, at 108.

According to the test method, it is important that data be gathered only after steady-state conditions have been determined for each pressure and velocity. With a sample mounted and the test system started, the temperature will increase and the coefficient of friction may vary for a specific pressure and velocity chosen until the heat energy dissipated is equal to the heat energy generated. After reaching steady-state operation, the load speeds and thermal conditions may be changed to develop data points for a three-dimensional wear model. The system monitors the load speeds and thermal conditions until it is determined that all of the conditions have reached steady-state. Upon reaching steady-state, the system monitors the displacement of the wear surface.

The wear rate is then calculated based upon the displacement of the wear surface during the steady state interval to calculate the wear rate for that specific pressure and velocity. For a particular pressure and velocity combination, the wear rate, coefficient of friction and temperature rise are recorded. The tribometer 10 then is incremented to a different pressure or velocity and the test interval is repeated. The changes in pressure or velocity may be done in small steps either by maintaining the pressure while increasing the velocity, by maintaining the velocity and increasing the pressure, or by modifying both to achieve the full three-dimensional wear map for the material.

Although a large number of pressure/velocity intervals are conducted, the system is capable of tracking as little as 10 nanometer displacement measurements, and the time to develop the three-dimensional pressure-velocity map is still considerably shorter than a traditional P-V model test. The system then calculates the characteristic coefficients of the material that can be exported to the common separated value (CSV) file for further graphing and analysis. Theoretical models of plain bearing behavior can be developed based upon the characteristic coefficients that describe the behavior of a plain bearing as represented by a three-dimensional map.

Other embodiments of the invention may incorporate lubrication systems including drip, spray or flood lubricant methods. The disk against which the test sample is loaded may be made of various bearing materials or sliding surface combinations. The disk may be replaced or changed to a different material to verify test results or provide a simulation of a bearing application.

A servo drive (not shown) and surface sensors (not shown) may be added to the cross slide to continuously move the contact surface onto a fresh area of the wear surface disk 18. The sensors (not shown) may measure the surface profile and actuate the servo drive (not shown) so as to position the test sample 28 on a surface with the appropriate surface characteristic as defined by the user. If the contact surface is moved onto a fresh area of the rotating disk, the disk speed may be varied to maintain a constant relative contact velocity even though the radius of the contact point on the disk has changed.

Referring to FIG. 1, the laser 30 may be one of two or three lasers that may be used to correct for noise factors in the test apparatus relating to thermal expansion, disk surface variations, deflection of the disk caused by the load applied through the specimen, or film transferred from the test specimen to the test surface. A second laser 80 may be supported on the same structure 12 as the first laser 30 but is directed to the wear surface 18 of a disk, or other work surface. The second laser 80 may be used to correct measurements of the first laser 30 by subtracting or otherwise comparing the measurement to the first laser measurement. Errors relating to the disk being not perfectly flat, the smoothness of the bearing surface, or thermal expansion may be corrected with the second laser 80.

The second laser 80 may be used to measure the thickness of a transfer film that may develop on the disk 18 that is transferred from the test specimen 28. In some tests, a thin film may be transferred from a test specimen to the test disk that can lead to inaccuracy in the displacement measurements. The third laser may be used to measure the thickness of the transfer film. If the transfer film is transparent, a laser may be used to measure two reflections, one off of the top surface and the other off of the back surface. The difference between the two measurements is the transfer film thickness.

The third laser 82 may also be used to develop a profile analysis utilizing a laser that projects a grid pattern or it may be a multiple beam laser displacement measuring system. One example of a test application that may benefit from profile analysis is a brake test that tests a sacrificial disk and rotor combination. The profile analysis can indicate the location of the contact area and may allow for the form of wear (plowing or abrasive) and rate of wear of the disk material and rotor material.

The tribometer 10 may be used to perform lubricant testing in a variety of simulated test combinations. The specimen and disk, or other wear surface, are selected and the test is begun by determining the location of a test sample with a first laser that is pressed onto a stationary disk with no oil between the test sample and the disk. A second laser determines the location of the stationary disk. The disk is then rotated at a selected velocity with the selected load applied. Oil may be sprayed, flooded, or provided by immersion from an oil sump 86, shown in FIG. 2. Rotation of the disk causes oil to be carried between the test sample and the disk that raises the sample. The displacement of the sample relative to the disk is measured to provide an accurate representation of film thickness.

The test continues with the tribometer dynamically measuring the thickness of the lubricant confined between or flowing through a space between the specimen and the wear surface. The specimen and wear surfaces may be moved in an oscillating, pivoting or rotational manner. Referring to FIGS. 1-3, one or more of the lasers 30, 80, or 82 may be reflected off of a surface associated with the test specimen 28 and the test surface 18 to measure the thickness of the lubricant film. The lubricant test method may be used to determine if the lubricant is in a hydrodynamic lubrication regime (floating), a mixed lubrication regime (minimum touching or contact), or a boundary layer lubrication regime (surfaces touching with measurable wear). If the film thickness remains constant, hydrodynamic lubrication is indicated. If there is a reduction in film thickness, the system may be used to determine the wear rate of the test specimen and test surface. The lubricant test may also be used in a rotating system such as the sleeve 18' and shaft 28', as shown in FIG. 4, with the film thickness being measured by lasers that are directed to a point diametrically opposite the lubricated contact point.

Figure 8:
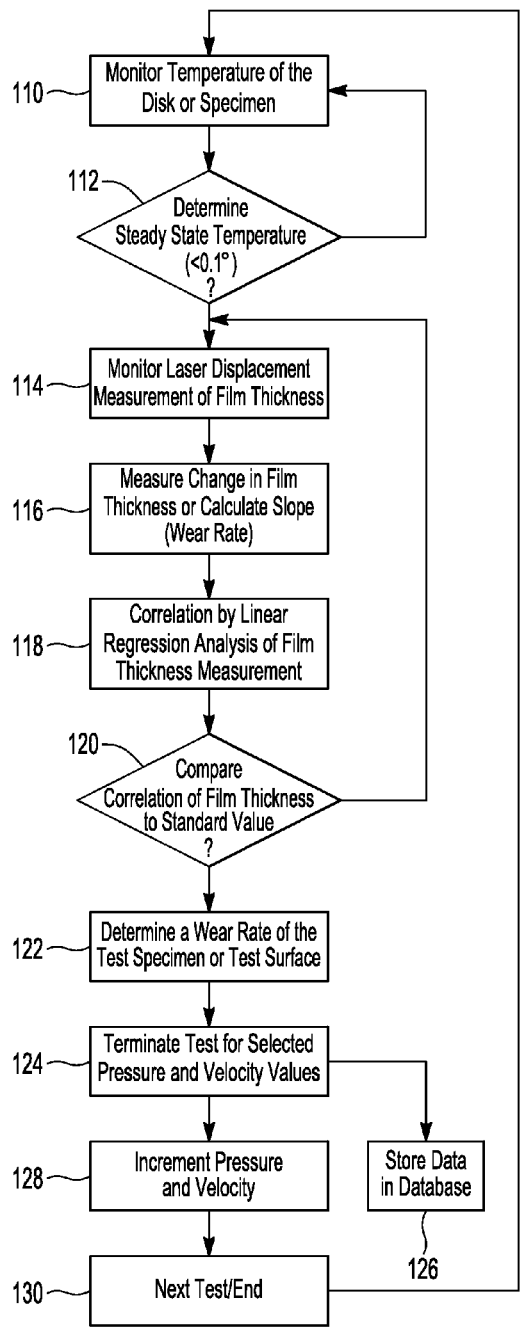
FIG. 8 is a flow chart illustrating one embodiment of a method of testing a lubricant.

Referring to FIG. 8, a lubricant test is illustrated by a flow chart that illustrates one example of a lubricant test. It should be understood that many other different test procedures may be developed within the spirit and scope of Applicant's invention. The lubricant test begins by monitoring the temperature of the disk or specimen, at 110. The system then determines, at 112, whether the temperature has reached steady state (for example, less than 0.1° C.). The system then monitors the laser displacement measurement of the film thickness, at 114, by determining the extent that the oil raises the test specimen. The film thickness is the thickness of the film as measured between the test disk and specimen with a selected load "P" that is moved at velocity "V" dynamically during the course of the lubricant test. The system measures changes in film thickness and may calculate a slope or wear rate, at 116. Simultaneously with measuring the change in film thickness, the system may correlate, at 118, by linear regression analysis or other dynamic mathematical analysis whether a constant film thickness is maintained or if there is a changing film thickness. The system compares, at 120, the correlation of film thickness to a standard value or regression coefficient. The system may determine a wear rate, at 122, of the test specimen or test surface. The system may terminate the test, at 124, for selected pressure or velocity values and the wear rate for each pressure and velocity value may be stored in a database, at 126. The system then may increment the pressure and velocity, at 128, to begin a test at a different pressure and/or velocity of the material. After incrementing at 128, the system moves to the next test, at 130, and returns to monitoring the temperature of the disk or specimen, at 110. Once all the selected pressures and velocities are tested, the test may end, at 130.

Lubricant testing may be applied to round or cylindrical test surfaces such as a shaft and a sleeve or a ball bearing and a race. A lubricant receptacle 84 that is diagrammatically illustrated in FIG. 2 may be filled with a lubricant to be tested or provided between wear surfaces to test materials in a lubricated environment. Lubricants may also be supplied in a spray or other form or air may be provided as a lubricant or coolant.

A lubricant may be tested under a variety of pressures and velocities dynamically with the same test procedure and apparatus. The tests may be automated to index to a new pressure and or velocity setting when either a steady state constant film thickness or a linear wear rate is determined.

As required, detailed embodiments of the present invention are disclosed. It is to be understood that the disclosed embodiments are merely examples of the invention that may be embodied in various and alternative forms. The figures are not necessarily to scale and some features may be exaggerated or minimized to show details of particular components. The specific structural and functional details disclosed are not to be interpreted as limiting, but merely as a representative basis for teaching one skilled in the art to make and use the present invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An apparatus for measuring a wear rate of a test specimen, comprising:
    a support structure;
    a test surface supported by the support structure;
    a test specimen supported by a sample holding fixture on the support structure and engaging the test surface to cause wear of the test specimen;
    a drive operatively engaging at least one of the test surface and the test specimen to move the other of the test surface and the test specimen relative thereto;
    a laser displacement measurement apparatus supported by the support structure that reflects a laser off of a surface of one of the sample holding fixture and the test specimen to measure displacement of the test specimen relative to the support structure as a result of the wear of the test specimen, wherein the laser displacement measurement apparatus is a first laser displacement measurement apparatus and a second laser displacement measurement apparatus is supported by the support structure that reflects a second laser off of a wear track formed on the test surface by the test specimen, wherein displacement measured by the first laser displacement measurement apparatus and second laser displacement measurement apparatus are compared to correct for noise factors in displacement measurements, and wherein the second laser displacement apparatus measures the thickness of a film transferred from the test specimen to the test surface, wherein the second laser displacement measurement apparatus measures a first reflection off of the top surface of the film and a second reflection off of the bottom surface of the film to determine a transfer film thickness to correct the measurement of the displacement of the test specimen; and
    a controller receives data as to the displacement of the test specimen relative to the support structure and data as to operation of the drive over time and is configured to measure the wear rate of the test specimen.

2. The apparatus of claim 1 wherein an optical profiling system is used to determine a profile of the wear track including a width and a depth of the wear track and is selected from the group comprising:
    a projection grid pattern system; or
    a multiple beam laser displacement system.

3. The apparatus of claim 1 wherein the test surface is a flat disk that is rotated in a first plane and the test specimen is moved by relative to the sample holding fixture and to the flat disk in a second plane that is parallel to the first plane.

4. An apparatus for measuring a wear rate of a test specimen, comprising:
    a support structure;
    a test surface supported by the support structure;
    a test specimen supported by a sample holding fixture on the support structure and engaging the test surface to cause wear of the test specimen;
    a drive operatively engaging at least one of the test surface and the test specimen to move the other of the test surface and the test specimen relative thereto;
    a laser displacement measurement apparatus supported by the support structure that reflects a laser off of a surface of one of the sample holding fixture and the test specimen to measure displacement of the test specimen relative to the support structure as a result of the wear of the test specimen; and
    a controller receives data as to the displacement of the test specimen relative to the support structure and data as to operation of the drive over time and is configured to measure the wear rate of the test specimen, wherein the support structure includes a load application system that applies a calibrated load P to the test specimen and the drive includes a variable speed control that moves the test surface at a calibrated speed V, and wherein displacement of the test specimen is recorded as a wear rate W, and wherein the calibrated load P is applied and the drive is operated at the calibrated speed V until the wear rate is determined to be at a steady state based upon dynamic mathematical analysis of P and V, wherein the wear rate value W is recorded for P and V, wherein the test specimen is subjected to a different combination of values P and V, repeatedly, and wherein mathematical analysis determines the correlation and reliability of the calculated values.

5. The apparatus of claim 4 wherein the test specimen is sequentially subjected to a plurality of loads P and a plurality of speeds V to develop a plurality of wear rates W that are mapped to develop a three dimensional wear rate map for a specimen.

6. The apparatus of claim 4 wherein the test specimen is sequentially subjected to a plurality of loads P and a plurality of friction values F that are mapped to develop a three dimensional friction map for a specimen.

7. The apparatus of claim 4 wherein the support structure includes a load application system that applies a calibrated load P to the test specimen and the drive includes a variable speed control that moves the surface at speed V, wherein energy E is calculated as P×V and a coefficient of friction value F.

8. The apparatus of claim 4 wherein the test surface is cylindrical in shape and wherein the drive rotates the test surface about an axis and wherein displacement of the test specimen and test surface is measured by the laser displacement measurement apparatus.

9. The apparatus of claim 4, wherein the test specimen is a cylindrical sleeve and the test surface is a cylindrical shaft within the cylindrical sleeve in an oscillating motion, and wherein displacement of the sleeve and shaft is measured by the laser displacement measurement apparatus.

* * * * *